United States Patent [19]

Van Dedem et al.

[11] Patent Number: 4,840,897

[45] Date of Patent: Jun. 20, 1989

[54] MODIFIED HUMAN INSULIN AND ITS USE AS STARTING MATERIAL FOR THE PREPARATION OF HUMAN INSULIN

[75] Inventors: Gijsbert W. K. Van Dedem; François E. A. Van Houdenhoven, both of Heesch, Netherlands

[73] Assignee: Akzo N.V., Arnhem, Netherlands

[21] Appl. No.: 767,481

[22] Filed: Aug. 20, 1985

Related U.S. Application Data

[63] Continuation-in-part of Ser. No. 485,592, Apr. 18, 1983, abandoned.

Foreign Application Priority Data

[30] Apr. 21, 1982 [NL] Netherlands ............... 8201650

[51] Int. Cl.$^4$ .............. C12P 21/06; C12P 21/02; C12P 21/04; C07K 7/40
[52] U.S. Cl. ......................... 435/69; 435/70; 435/71; 530/303
[58] Field of Search ............... 435/68, 69, 70, 212, 435/219, 224, 71; 530/303

[56] References Cited

U.S. PATENT DOCUMENTS

| | | | |
|---|---|---|---|
| 3,276,961 | 10/1966 | Bodansky et al. | 435/70 |
| 4,182,654 | 1/1980 | Royer | 435/70 |
| 4,320,196 | 3/1982 | Morihara et al. | 435/70 |
| 4,320,197 | 3/1982 | Morihara et al. | 435/70 |
| 4,343,898 | 8/1982 | Markussen | 435/70 |
| 4,639,332 | 1/1987 | Grau | 530/303 |
| 4,645,740 | 2/1987 | Breddam et al. | 435/71 |

FOREIGN PATENT DOCUMENTS 0045187 2/1982 European Pat. Off. ............. 435/71

OTHER PUBLICATIONS

Breddam, K. et al, Carlsberg Research Communications, vol. 46, pp. 361–372, 1981.

K. Morihara et al, "Semi–Synthesis of Human Insulin by Trypsin Catalysed Replacement of Ala–B30 by Thr in Porcine Insulin", Nature, vol. 280, No. 5721, Aug. 1979, pp. 412–413.

K. Morihara et al, "Synthesis of Human Insulin. Semi–Synthesis from Swine Insulin with High Yield", Chemical Abstracts: vol. 95, No. 5, 1982, p. 331.

K. Morihara et al, "Achromobacter Protease I–Catalyzed Conversion of Porcine Insulin into Human Insulin", Biochem and Biophys Research Communications, vol. 92, pp. 396–402, 1980.

*Primary Examiner*—Jayme A. Huleatt
*Attorney, Agent, or Firm*—William M. Blackstone

[57] ABSTRACT

A novel modified human insulin of the general formula:

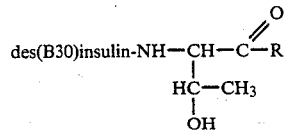

wherein R is a hydrophobic or charged amino acid or a di- or tripeptide group, comprising a hydrophobic or charged amino acid or an amide or ester of said amino acid or peptide and its use as starting material for the preparation of human insulin.

6 Claims, No Drawings

MODIFIED HUMAN INSULIN AND ITS USE AS STARTING MATERIAL FOR THE PREPARATION OF HUMAN INSULIN

This application is a continuation-in-part of Ser. No. 485,592, now abandoned filed Apr. 18, 1983.

The present invention is concerned with a novel modified human insulin and its use as starting material for the preparation of human insulin.

It is known to prepare human insulin from animal insulin in order to avoid antigenic or allergenic reactions, which occur in certain cases if animal insulin is administered to insulin deficient human beings. It is known as well to use those animal insulins for the preparation of human insulin which show the smallest difference with human insulin with respect to amino acid sequence. Particular use is made of insulins isolated from the pancreas of pigs or cattle and more in particular of pigs. Pig and human insulin, for example, differ in one amino acid, namely the carboxy-terminal amino acid of the so-called B-chain. This so-called B30 amino acid is alanine in pig insulin but threonine in the human. Pig insulin could therefore be converted into human insulin by replacing this B30 amino acid by threonine and a number of methods are known for doing so.

Nearly all known methods of course start by removing the B30 amino acid: in the case of pig insulin, the alanine is therefore removed. This produces des(B30)insulin, also often called des(Ala)insulin, DAI in brief. For subsequent processes, a number of alternative methods are known which lead to the formation of human insulin. These are based on the enzymatic or non-enzymatic bonding of threonine, in which the carboxyl group is protected, in order to obtain a modified human insulin and on the subsequent removal of the protecting group.

U.S. Pat. No. 4,320,196 (Morihara et al.) discloses, inter alia, the use of alkyl groups and in particular of tertiary butyl groups as the protecting group. These modified human insulins according to Morihara exhibit a poor separation performance with respect to the material where they are made from, the des(B30)insulin, particularly during large-scale preparation, except at the expense of very heavy losses. The protecting group is removed according to this Morihara reference under quite drastic conditions, particularly an extreme pH, affecting the quality of the human insulin obtained because of partial degradation of insulin, giving degradation products which are virtually inseparable from the insulin.

Surprisingly, a novel modified human insulin has been found which exhibits an improved performance regarding the separation from the material where it is made from and which is very suitable as starting material for the preparation of human insulin under mild conditions by applying enzymatic treatment known as such.

Accordingly the present invention is dealing with modified human insulin of the formula I

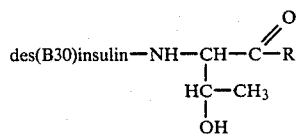 (I)

wherein R is an amino acid or peptide, or an ester or amide of said amino acid or peptide group and with its use as starting material for the preparation of human insulin by enzymatic treatment.

The modified human insulin as described in formula I can conveniently be prepared by bonding to des(B30)insulin the compound II

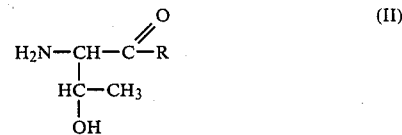 (II)

or by bonding to des(B29,B30)insulin the compound III

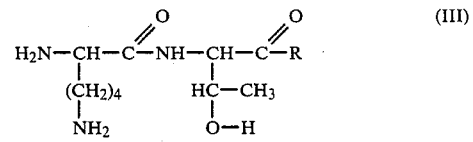 (III)

wherein R in both compounds has the meaning described above.

Des(B30)insulin can be prepared separately by treating animal insulin, which is apart from the B30 amino acid on all points identical with human insulin, with a suitable enzyme, e.g. with carboxypeptidase A, or with lysylendopeptidase from *Achromobacter lyticus*. A des(B30)insulin residue can be prepared in situ, however, in which case the removal of the B30 amio acid and the bonding of the compound II are achieved in a so-called transpeptidase reaction by a single enzyme, e.g. trypsine.

Des(B29,B30)insulin can likewise be prepared from a suitable animal insulin using a dipeptidase, or using a peptidase which specifically cleaves the proline-lysine peptide bond.

The compound II may be bonded to the B29-lysine of the previously prepared des(B30)insulin with e.g. the aid of trypsine or with any other enzyme with trypsine-like effect, such as lysylendopeptidase. Carrier linked enzymes may be used, in which case enzyme and solution with modified insulin can be separated simply after the reaction has ended. The pH applied during the formation of the modified human insulin according to the present invention may range from 5–9, preferably from 6–7. Reaction temperature may be conveniently chosen from 0° C. to 50° C. and preferably from 20° C. to 45° C., 37° C. being the optimal temperature. The reaction time may vary widely and will generally lie between 10 min. and 50 h. Preference is given to a reaction time of ¼–5 h. The concentration of the des(B30)insulin or the des(B29,B30)insulin may conveniently be chosen between $2.10^{-4}$ and $2.10^{-2}$ mol/l and preferably between $1.10^{-3}$ and $1.10^{-2}$ mol/l. The molar rato of des(B30)insulin and compound II and of des(B29,B30)insulin and compound II should be at least 1:2 and preferably at least 1:5. The reaction mixture generally comprises 40–80% v. of organic fraction. Preference is given to the preparation of the novel modified human insulin from des(B30)insulin.

The novel modified human insulin obtained can be separated easily from the des(B30)insulin or des(B29,B30)insulin and is very suitable as starting material for the preparation of human insulin by enzymatic treatment of the modified human insulin.

The group R in the formula representing the modified human insulin is an amino acid or peptide group, or an amide or ester of said amino acid or peptide group. If R is a peptide group or amide or ester thereof the amino acids in the peptide group preferably are the same. Preference is given to an amino acid, dipeptide or tripeptide or an ester or amide thereof.

The choice of the amino acids in group R is governed by two aspects: in the first place the ΔRf for the modified human insulin with respect to the des(B30)insulin should be as large as possible and in the second place the group R should be removed as selectively as possible by enzymatic treatment under mild conditions. In view of this preference is given to phenylalanine, tryptophan, valine, leucine, isoleucine, arginine, lysine, aspartic acid and glutamic acid; more preference is given to phenylalanine, tryptophan, arginine and lysine and the most preference to phenylalanine.

The separation of the modified human insulin from the des(B30)insulin may be conducted by peptide separation techniques known in the art. Preferably the separation is conducted by means of chromatography.

If hydrophobic amino acids are applied, purification is strongly promoted under hydrophobic conditions, whereas separation and purification under polar or ionizing conditions are improved on bonding charged amino acids.

In order to prepare human insulin, the residual group R must be removed enzymatically from the modified human insulin with the general formula I. The choice of residual group determines which enzyme or which combination of enzymes is suitable for this purpose.

In general group R can be advantageously removed with the aid of a carboxypeptidase. A carboxypeptidase is an exopeptidase which can remove one amino acid after the other from the peptide chain starting from the carboxy terminal, showing preference for certain amino acids.

Carboxypeptidase A (CPA), for instance, splits off hydrophobic amino acids in particular with a preference for phenylalanine and tryptophan and carboxypeptidase B (CPB) preferably splits off basic amino acids. Other carboxypeptidases or dipeptyl carboxypeptidases may be used as well. The choice of the enzyme is dependent on the group R in the modified human insulin. The method of enzymatically separating one or more amino acids from a peptide by means of carboxypeptidase is known as such. For the preparation of human insulin from the modified human insulin according to the present invention the pH may range from 5-10 and preferably from 6-9, the reaction time from 10 min. to 10 h. and preferably from 20 min. to 5 h., the temperature from 0°–50° C. and preferably from 20°–45° C. and the amount of enzyme from 1-500 U per g modified human insulin and preferably 1-250 U per g modified human insulin.

The invention can be further illustrated by means of the following examples.

In the following examples, des(B30)insulin is used as a basis in each case, prepared from pig insulin according to the method described by E. W. Schmitt et al. (Hoppe Seyler's Z. Physiol. Chemie 359, 799 (1978), the so-called des(ala)insulin (DAI).

EXAMPLE I-VIII

Bonding of di- and tripeptide to DAI

The bonding is undertaken with various substrata (di- and tripeptides and HCl-salt of tripeptide) with various enzyme systems (trypsine, and carrier-linked trypsine and lysylendopeptidase).

These bondings are undertaken as follows:
(a) A buffer medium is composed from
 a 1:1 mixture of dimethylformamide with ethanol (=the so-called organic fraction) and
 a certain quantity of tris HCl buffer with concentration $0.5$ mol.l$^{-1}$.
(b) A weighted quantity of substratum is dissolved in this buffer medium together with a quantity of DAI.
(c) This mixture is raised to the desired pH by means of concentrated NaOH (1 mol.l$^{-1}$).
(d) A quantity of the bonding enzyme is added, after which, the bonding reaction commences and which then continues at 37° C.
(e) On completion of the reaction period, the reaction product is separated chromatographically; the yield of the bonding product is determined from the chromatogram, and is expressed as a percentage of the theoretical value.

The reaction conditions and yield for examples I-VIII appear in Table 1.

TABLE 1

| | example nr. | | | | | | | |
|---|---|---|---|---|---|---|---|---|
| conditions | I | II | III | IV | V | VI | VII | VIII |
| concentration DAI (g · l$^{-1}$) | 67.1 | 66.6 | 13.6 | 25.2 | 32.2 | 32.2 | 58.2 | 40.7 |
| substrate | thr—phe | thr—phe | thr—phe—phe | thr—phe—phe—HCl | thr—phe—phe—Hcl | thr—phe phe | thr—phe—O—methyl methyl | thr—phe—phe—O— |
| concentration (mol · l$^{-1}$) | 0.176 | 0.175 | 0.037 | 0.047 | 0.025 | 0.4 | | 1.0 |
| | | 0.067 | | | | | | |
| enzyme (g · l$^{-1}$) | | | | | | | | |
| trypsine: | 2.7 | | 5 | | | | 1.8 | 3.2 |
| trypsine: silica: | | 808 | | | 157 | 157 | | |
| lysylendo-peptidase silica: | | | | 77 | | | | |
| medium (% organic fraction) | 60 | 60 | 67 | 60 | 60 | 60 | 60 | 60 |
| pH | 6.2 | 6.5 | 6.5 | 6.3 | 6.5 | 6.5 | 6.8 | 6.6 |
| reaction time (hours) | ½ | 1 | 7/12 | 48 | 3 | 3 | 3 | 1 |
| yield | 53 | 28 | 54 | 38 | 27 | 16 | 23 | 86 |

TABLE 1-continued

| | example nr. | | | | | | | |
|---|---|---|---|---|---|---|---|---|
| | I | II | III | IV | V | VI | VII | VIII |
| conditions (% of theor.) | | | | | | | | |

EXAMPLE IX

Chromatographic separation of bonding products

A comparison has been made of the chromatograhic behavior of peptide bonded DAI with that of ester bonded DAI.

For this purpose, the bonding products of DAI with thr-O-methyl, thr-O-tBu, thr-phe-O-methyl thr-phe-phe and thr-phe-phe-O-methyl, are prepared in a similar way as described in the previous examples.

The bonding conditions were: DAI concentration 14 g.l$^{-1}$, 0.06 mol.l$^{-1}$ substratum, 2.5 g.l$^{-1}$ trypsine, 67% organic fraction in medium pH 6.4 and a reaction period of half an hour.

The bonding products were separated on an analytical HPLC column and the retention values (Rf) determined. The results of this separation appear in Table 2 as the difference in retention value of the bonding products from those of DAI (ΔRf).

TABLE 2

| Coupled to DAI | ΔRf (sec) |
|---|---|
| thr—O—methyl | 220 |
| thr—O—tBu | 1000 |
| thr—phe—O—methyl | 1400 |
| thr—phe—phe | 1700 |
| thr—phe—phe—O—methyl | 2200 |

As can be seen the separation performance of the modified human insulin according to the present invention from the DAI is superior over the modified human insulin according to the prior art. In this way DAI-thr-phe-phe and DAI-thr-phe-phe-O-methyl may be prepared having a purity of more than 99%.

EXAMPLE X

Removal of bonded group phe-phe from DAI-thr-phe-phe

After separating unconverted DAI and bonding product DAI-thr-phe-phe on a hydrofobic column, a fraction of 23 ml was obtained which contained 0.85 mg.ml$^{-1}$ bond product. This bonding product was freeze-dried and then dissolved in 0.2 mol.l$^{-1}$ ammoniumbicarbonate buffer pH 8.5 to a final concentration of approx. 2.8 mg.ml$^{-1}$. To this solution 2 μl carboxypeptidase A was added 2.3 E). The reaction was stopped after 30 minutes by adding an equal, volume of 0.5 mol.l$^{-1}$ citric acid. The material was then crystallized.

Examination showed that the bonding product has been completely converted to human insulin as demonstrated with the aid of amino acid analysis. After crystallisation, no other amino acids than phenylalanine could be demonstrated in the supernatant with the aid of amino acid analysis.

Experiments with DAI-thr-phe-O-methyl and DAI-thr-phe-phe-O-methyl under similar conditions revealed the same results.

As can be seen the removal of group R can be achieved very specifically. Hence a very pure (more than 99%) human insulin can be obtained with very high yield (more than 99%).

We claim:

1. Modified human insulin of the formula:

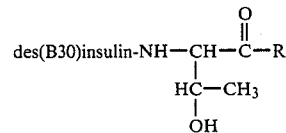

wherein R is selected from the group consisting of a hydrophobic amino acid, a charged amino acid, a dipeptide or a tripeptide wherein at least one of the amino acids is a hydrophobic or charged amino acid, an amide of said amino acid, dipeptide or tripeptide and an ester of said amino acid, dipeptide or tripeptide.

2. Modified human insulin as claimed in claim 1, wherein R is selected from the group consisting of a monomer of phenylalanine, a dimer of phenylalanine, or a trimer of phenylalanine, as ester of said monomer, dimer or trimer and an amide of said monomer, dimer or trimer.

3. Method for the semi-synthetic preparation of human insulin comprising (a) enzymatically bonding des-B30-insulin to a peptide comprising 2 to 4 amino acids or the amide or ester thereof, wherein the N-terminal amino acid is threonine, of the formula:

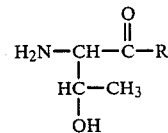

or enzymatically bonding desB29, B30-insulin to a peptide comprising 3 to 5 amino acids or the amide or ester thereof, wherein the N-terminal dipeptide is lysine-threonine, of the formula:

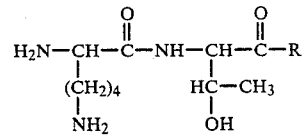

wherein R is selected from the group consisting of a hydrophobic amino acid, a charged amino acid, a dipeptide or a tripeptide wherein at least one of the amino acids is a hydrophobic or charged amino acid, an amide of said amino acid, dipeptide or tripeptide and an ester of said amino acid, dipeptide or tripeptide, to form the modified human insulin of claim 1, (b) isolating the modified human insulin (c) enzymatically removing R from the isolated modified human insulin and (d) thereafter isolating the resulting human insulin, wherein selection of enzymes in step (a) and step (c) is dictated by the peptide and by R, respectively, and wherein isolation of the modified human insulin in step (b) is conducted under hydrophobic conditions if the amino acids in the peptide are hydrophobic and under polar or ionizing conditions if the amino acids in the peptide are charged.

4. Method as claimed in claim 3 wherein R is selected from the group consisting of a monomer of phenylalanine, a dimer of phenylalanine, or a trimer of phenylalanine, an ester of said monomer, dimer or trimer and an amide of said monomer, dimer or trimer.

5. Method as claimed in claim 3, wherein the enzymatic removal of R is conducted by means of a carboxypeptidase selected with respect to the ionic character of R.

6. Method as claimed in claim 5, wherein the carboxypeptidase used is carboxypeptidase A.

* * * * *